United States Patent [19]

Lessnig et al.

[11] 4,361,032
[45] Nov. 30, 1982

[54] APPARATUS FOR MEASURING SURFACE TENSION

[75] Inventors: Werner Lessnig; Günter Metz, both of Cologne; Willi Spiegel, Leverkusen; Manfred Faust, Bergisch Gladbach; Günter Junkers, Leverkusen, all of Fed. Rep. of Germany

[73] Assignee: Agfa-Gevaert Aktiengesellschaft, Leverkusen, Fed. Rep. of Germany

[21] Appl. No.: 186,696

[22] Filed: Sep. 12, 1980

[30] Foreign Application Priority Data

Sep. 17, 1979 [DE] Fed. Rep. of Germany ....... 2937476

[51] Int. Cl.³ ............................................. G01N 13/02
[52] U.S. Cl. ................................................. 73/64.4
[58] Field of Search ......................................... 73/64.4

[56] References Cited

U.S. PATENT DOCUMENTS

| 2,473,553 | 6/1949 | Stokes | 73/64.4 |
| 4,228,677 | 10/1980 | Olsson et al. | 73/64.4 |

FOREIGN PATENT DOCUMENTS

| 2915957 | 11/1980 | Fed. Rep. of Germany | 73/64.4 |
| 55-24670 | 2/1980 | Japan | 73/64.4 |

Primary Examiner—S. Clement Swisher
Assistant Examiner—Joseph W. Roskos
Attorney, Agent, or Firm—Connolly and Hutz

[57] ABSTRACT

An apparatus for automatically determining the surface tension by the stalagmometer principle using a pipette containing a test volume, having a drop face at its lower end and is provided with three light barriers. The three light barriers are connected to an evaluation circuit which counts the number of whole drops and also determines the fractions of whole drops pertaining to the test volume.

3 Claims, 3 Drawing Figures

APPARATUS FOR MEASURING SURFACE TENSION

The invention relates to an apparatus for automatically determining the surface tension of liquids by the stalagmometer principle.

A plurality of measuring method and apparatuses for measuring surface tension $\sigma$ (N/m) are known. The relatively simple "stalagmometer measuring principle" of J. Traube (Traube, J. In Abderhalden, Handbuch der biochemischen Arbeitsmethoden, Volume V. Part 2, 1912, pages 1357 to 1370; Houben-Weyl, Methoden der Organischen Chemie, Volume III, Part 1, 1958, pages 468 to 471), is widely adopted.

The stalagmometer employed by J. Traube is similar to a transfer pipette whose outlet is shaped as a dropping face. Drops whose volume depend on the surface tension of the liquids to be examined are formed in succession on this polished face as the test liquid issues from the filled pipette. The higher the surface tension, the greater the volume of the drop and vice versa. The volume of the pipette is defined by ring markings. Line divisions (fine scales) with whose aid fractions of drops can be assessed are located above and below these ring markings. As the test volume of the pipette is constant and the volume of the individual drop depends on the surface tension, the number of drops formed from this constant test volume is a direct gauge of the surface tension. The determination of surface tension is thus restricted to the counting of drops which are formed from a definite volume. The measured number of drops is compared with the number of drops of pure water of known surface tension. The following equation then applies:

$$\sigma_X = \frac{\sigma_{H_2O} \cdot T_{H_2O}}{T_X} \cdot \frac{\rho_X}{\rho_{H_2O}}$$

in which
$\sigma_{H_2O}$ = surface tension of water at temperature t,
$T_{H_2O}$ = number of drops of water at temperaure t,
$\rho_{H_2O}$ = density of water at temperature t,
$T_X$ = number of drops of the liquid to be examined at temperature t,
$\rho_X$ = density of the liquid to be examined at temperature t.

The fraction $$\frac{\sigma_{H_2O} \cdot T_{H_2O}}{\rho_{H_2O}}$$

is an instrument constant which is determined by the dimensioning of the stalagmometer and is calculated once from the known literature values of $\sigma_{H_2O}$ and $\rho_{H_2O}$ (at temperature t) as well as the measured number of drops $T_{H_2O}$ (also at temperature t).

When performing a measurement using the stalagmometer, the following should be taken into consideration. According to Traube, correct measured values are only achieved for the surface tension if the speed of passage is established at a maximum of 20 drops per minute, i.e. a drop formation time of a minimum of 3 seconds per drop, irrespective of viscosity of the sample liquid. This is achieved by selecting suitable slowing-down capillaries which either slow down the passage of liquid directly beneath the test volume due to their flow resistance or achieve the slowing down effect above the test volume by curbing the air supply (ventilation). In practice, drop formation times of from 3 to 5 seconds are adopted.

As the surface tension is temperature dependent, it is essential for the stalagmometer to be thermostatically controlled.

Despite the relaively simple measuring principle, the known stalagmometer has substantial disadvantages. The main disadvantage is the limited accuracy of measurement due to visual reading of ring and line markings. As the fall of the first and last drop to be counted does not generally coincide exactly with the passge of the upper and lower ring markings, fractions of drops have to be determined by means of a line scale arranged above and below the ring markings. An increase in the accuracy of measurement demands a larger test volume, resulting in a larger number of drops which then leads to disadvantageous prolonged measuring times. With the known stalagmometer the test volume, for example, is dimensioned in such a way that a drop number of about 55 drops is obtained in the case of water at 20° C. In the case of liquids having a low surface tension, this leads to numbers of drops somewhat exceeding 100. Disadvantageously long measuring times of more than 300 seconds result from these high drop numbers.

Another disadvantage arises from the purely manual handling as well as the reading and evaluation of the measured values. Measurement is, therefore, very labour intensive and demands qualified, responsible operators as the possibilities for subjective errors are otherwise too great.

These disadvantages result in another significant disadvantage that of its applicability being stricted to intermittent laboratory measurement only. Routine measurement by operators or almost continuous measurement i.e. measurement which is automatically cyclically consecutive, cannot be carried out in the monitoring of operations.

An object of the invention is to increase the accuracy of measurement in an automated apparatus for measuring the surface tension by the stalagmometer principle and simultaneously to minimise the measuring time.

This object is achieved according to the invention in that the test volume of the pipette is restricted by an upper and lower light barrier, and an additional light barrier is arranged below the dropping face, and the three light barriers communicate with an evaluating circuit which counts the number of T0 of whole drops originating from the test volume and appearing at the drop face and also determined the fractions T1, T2 of whole drops pertaining to the test volume during passage of the liquid meniscus through the upper and lower light barriers from the pulse trains occurring at the three light barriers.

According to a preferred embodiment of the invention, an electronic evaluating circuit consisting of the following units is provided for this purpose:

(a) an electronic time counter which is connected by circuitry to the three light barriers;
(b) a store unit connected to the time counter in which the following conditions are stored:
1. the time counter state Z1 corresponding to the last drop N before the response of the upper light barrier;

2. the time counter state Z2 corresponding to the passage of the meniscus through the upper light barrier;
3. the time counter state Z3 occurring at the upper light barrier after passage of the next drop N+1;
4. the number T0 of whole drops detected during the outflow occurring after the drop N+1 has run out of the test volume at the drop face by the light barrier located beneath it;
5. the time counter state Z4 corresponding to the last drop N+1+T0 before the response of the lower light barrier;
6. the time counter state Z5 corresponding to the passage of the meniscus through the lower light barrier;
7. the time counter state Z6 connected to the lower light barrier after passage of the subsequent drop N+1+T0+1, (c) and a computer which forms the quotients $$T1 = \frac{Z3 - Z2}{Z3 - Z1} \text{ and}$$

$$T2 = \frac{Z5 - Z4}{Z6 - Z4}$$

from the stored time counter states and then forms the sum $T_x$ of the whole drop T0 and fraction of drops T1 and T2 which have issued from the test volume in order to detect fractions of a whole drop.

The actual time values of the time counter Z1 to Z6 are thus allocated to the drops immediately before and after the response of the light barriers as well as the passages of the meniscus through the light barriers, and stored. The whole drops T0 contained in the volume between the light barriers are detected by the light barrier arranged below the drop face and are also stored. If one were to calculate the surface tension using this value for the number of drops, fairly great measuring errors would thus be produced as the test volume does not generally represent an integral multiple for the number of drops. The error in measurement corresponds to the undetected fractions of drops in the region of the upper and lower light barrier (up to −2 drops). These fractions of drops can, however, be taken into account in the manner described above by evaluating the time values Z1 to Z6 stored in the electronic store. By adding the number of whole drops T0 and the fractions of drops T1, T2, the exact number $T_x$ of drops contained in the test volume is produced.

The objective detection of fractions of drops represents a substantial improvement in the accuracy of measurement. Nevertheless, with the known stalagmometers, the test volume and therefore the number of drops has to be selected relatively large so that the percentage error of measurement due to the undetected fractions of drops remains smaller. However, a large test volume has the disadvantage of a very long measuring time as the number of drops and thus the issuing time is correspondingly large. Accordingly, for the first time, the invention meets the requirements of reducing the test volume of the stalagmometer and this the number of drops, without impairing the accuracy so that substantially shorter measuring times are obtained. The short measuring times allow almost continuous, i.e. cyclically successive measurement of the surface tension of, for example, processing streams. A further development of the invention consequently proposes that a flow vessel through which the sample liquid continuously flows be arranged beneath the drop face of the stalagmometer.

Another advantage of the apparatus according to the invention is achieved by arranging the three above-mentioned light barriers in such a way that their signals are used in conjunction with a subsequent electronic control circuit for the automatic control of the apparatus so that the entire measurement process is completely automated and can be repeated cyclically in a predetermined manner once the sample has been inserted manually into the apparatus. The value of the surface tension $\sigma$ is emitted directly in N/m by feeding in density in g per cm$^3$ and the predetermined instrument constant via an input/output unit into the electronic circuit arrangement.

The advantage described are of great importance with respect to routine measurement by unqualified operators.

An embodiment of the invention is described in more detail below with reference to drawings.

Figure 1:
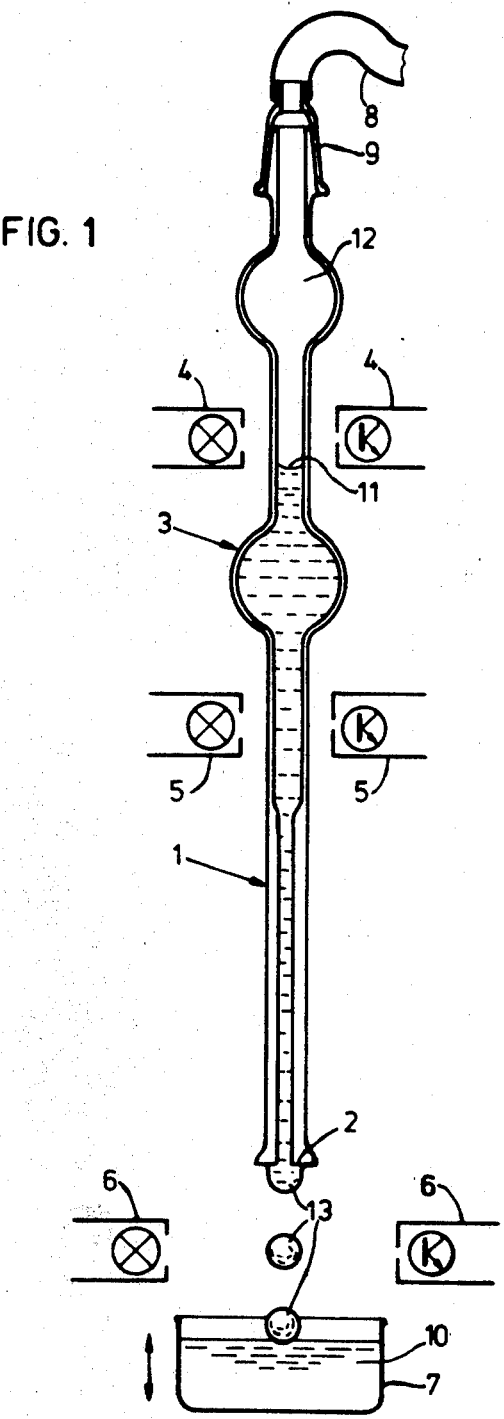
FIG. 1 shows the fundamental structure of a stalagmometer.

According to FIG. 1, the stalagmometer consists of a pipetter 1 with a drop face 2. Instead of the conventional ring markings the light barriers 4 and 5 are arranged above and below a spherical widening at cylindrical tubes. They define the test volume 3. Another light barrier 6 is located beneath the drop face 2. A sample container 7 which can be shifted in height is arranged beneath the drop face 2. A retarding capillary is located in a pneumatic unit (not shown) of the automated stalagmometer and is connected via tube connection 8 and ground section 9 to the pipette 1. The measuring process begins with the filling of the pipette 1. The sample supply container 7 is first raised sufficiently to allow the drop face 2 to be immersed completely in the sample liquid 10. The sample liquid 10 is sucked into the pipette 1 by applying a vacuum via the tube connection 8. Once the liquid meniscus 11 has passed the upper light barrier 4, the suction process is stopped after a time delay and the sample container 7 is lowered back into its starting position. The sample liquid 10 is now located in the volume 12. The pipetter 1 is then ventilated via the retarding capillary in the pneumatic unit and drops 13 form on the drop face 2. The drops break from the drop face 2 in succession, pass through the light barrier 6, cause a response pulse in the subsequent electronic circuit arrangement and fall into the sample container 7. In this process, the liquid meniscus 11 successively passes through the upper light barrier 4 and the lower light barrier 5 and thus also produces one response pulse in each case in the circuit arrangement. The measurement process is completed once the next falling drop 13 has passed the light barrier 6 after the response of the lower light barrier 5. Other measurements can be added cyclically, depending on the programming of the electronic circuit arrangement.

Figure 2:
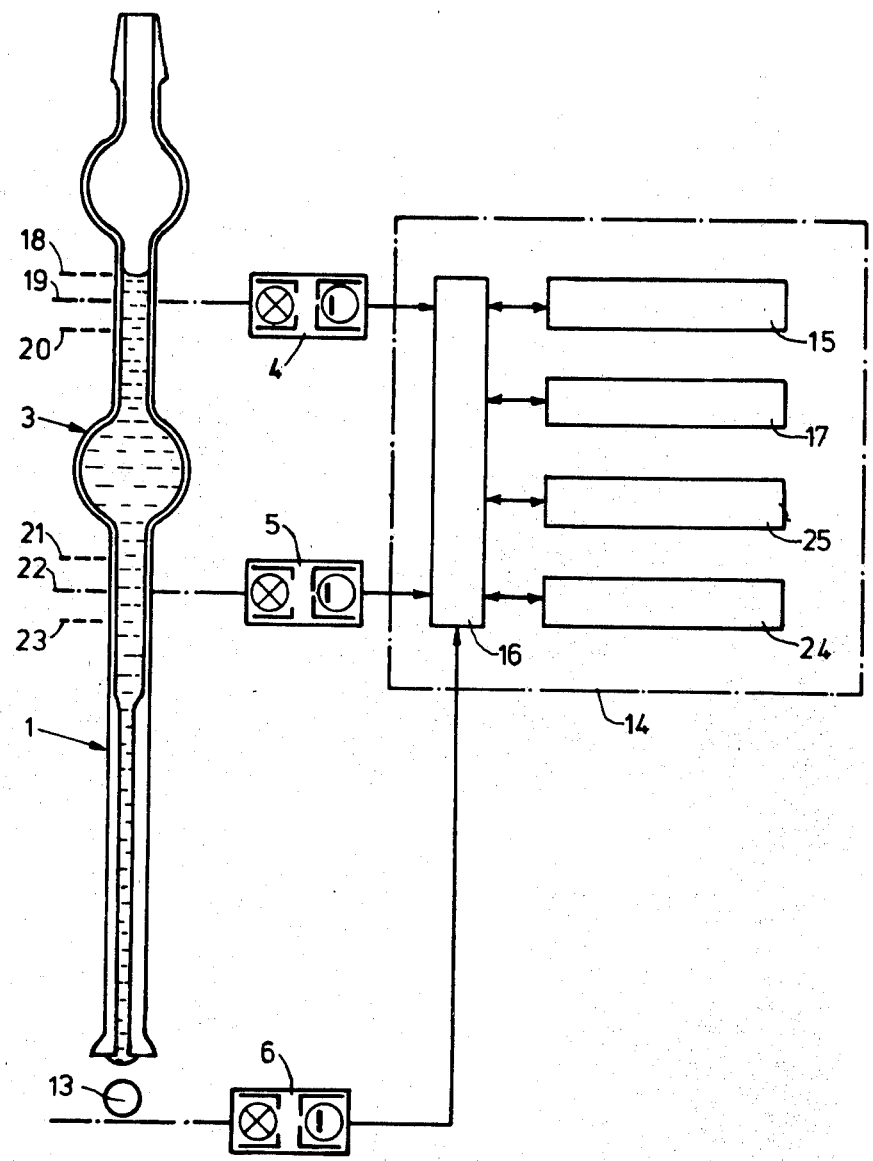
FIG. 2 shows the centre piece of the stalagmometer with the light barrier planes and schematically shows an associated electronic circuit arrangement for detecting and processing the light barrier signals.
Figure 3:
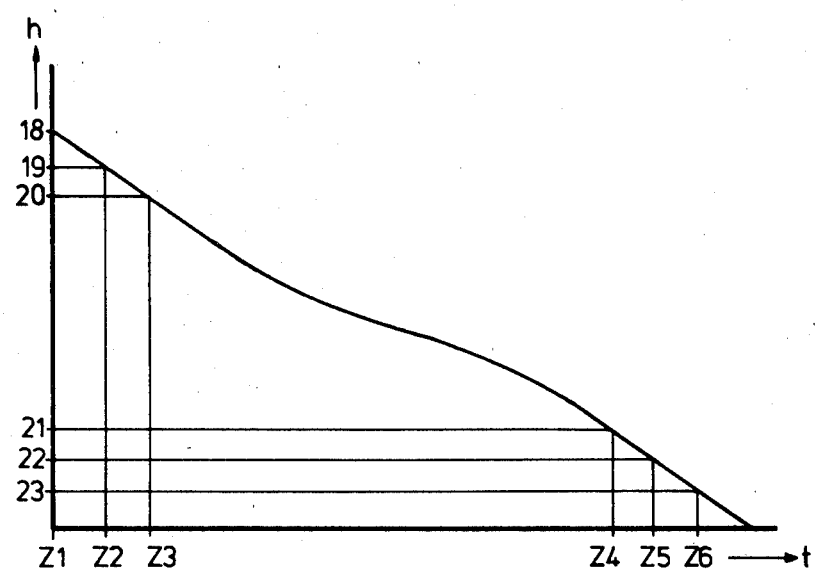
FIG. 3 shows the meniscus level in the stalagometer during the measuring process as a function of time.

FIG. 2 shows the detection and processing of the signal. In an electronic circuit arrangement 14 (evaluation circuit) a readable time counter 15 which runs continuously during the entire measuring process, is started at the beginning of the dropping process upon completion of the filling process. The present state of the time counter is scanned by the control device 16 during each response of the three light barriers 4 or 5 or 6 and stored in the store 17. Before the response of the upper light barrier 4, the preceding time counter state is over-written with each drop 13 passing the light barrier 6. The meniscus level 18 with the time counter state Z1 corresponds to the last drop N before the response of the upper light barrier 4. The meniscus level 19 with the time counter state Z2 corresponds to the subsequent response of the upper light barrier 4. The next drop falls during the meniscus state 20 with the time counter state Z3. The time counter states Z1, Z2 and Z3 are thus linked respectively to the liquid meniscus levels 18, 19 and 20. The fall of the drops immediately before and after the meniscus passage are thus allocated to the meniscus passage through the upper light barrier 4. In accordance with the upper light barrier 4, the time counter states Z4, Z5 and Z6 are linked to the respective levels of the liquid meniscus 21, 22 and 23 at the lower light barrier 5. The fall of the drops immediately before and after the meniscus passage are thus allocated to the meniscus passage through the lower light barrier 5. This is further clarified by the flow graph shown in FIG. 3. The graph shows the meniscus level h in the stalagmometer as a function of the time i.e. during the measuring process. The level of the liquid (meniscus level) falls from the level 18 beyond the light barrier level 19 and the level 20 located beneath it linearly with time to a first approximation. The change of level from 18 to 20 corresponds to the volume of a whole drop. About half a drop cannot be counted without taking the fractions of drops into consideration. After passing through the upper light barrier 4, the meniscus enters the spherical volume. Due to the larger diameter, the fall rate decreases toward the centre of the sphere and then increases again approximately to the original value. The meniscus finally reaches the lower light barrier 5. The meniscus level 21 is achieved just before the last drop leaves the test volume 3. However, FIGS. 2 and 3 show that, as with the first drop pertaining to the test volume, the whole drop no longer pertains to the test volume but only a fraction (about half) i.e. the part lying between the levels 21 and 22.

On the other hand, the portion of the drop lying between the level 22 and 23 no longer pertains to the test volume. The time markings Z4, Z5 and Z6 correspond to the passage of the meniscus through the levels 21, 22 and 23 in the region of the lower light barrier 5.

The number of whole drops T0 which are formed from the volume between the meniscus levels 20 and 21 is counted by the light barrier 6. The fractions of drops T1 and T2 produced from the volume between the meniscus levels 19 and 20 as well as 21 and 22 are determined from the time counter states Z1 to Z6 stored in the store 17 in the following manner by means of the control device 16 in the computer 24.

The fraction of a drop T1 between the meniscus levels 19 and 20 is the quotient of the differences between the time counter states Z3-Z2 and Z3-Z1, the fraction of the drop T2 between the meniscus levels 21 and 22 is the quotient of the differences between the time counter states Z5-Z4 and Z6-Z4. The fractions of drops T1, T2 pertaining to the test volume 3 are thus determined on the basis of the relationship between the meniscus level and time in the region of the upper light barrier 4 and lower light barrier 5 which is linear to a first approximation (see FIG. 3). The number of drops $T_x$ which form as the sample liquid flows out of the test volume 3 of the stalagmometer, limited by the light barriers 4 and 5, is obtained by adding the whole drops T0 and the fractions of drops T1 and T2. This the accuracy of the fractions of drops calculated depends on the ratio of the drop frequency to the counting frequency of the time counter 15. The frequency ratio must be $\geq 1:10$ for the necessary accuracy of $\pm 0.1$ drops, with mathematical rounding of the fractions of drops. The Test volume 3 is adapted to the accuracy requirements of the test result, i.e. whole drops plus fractions of drops, in order to optimise the measuring time. Thus, for example, with an accuracy requirement of $\pm 1\%$, corresponding to an accuracy of $\pm 0.1$ drops, the test volume 3 should be selected in such a way that at least 10 drops 13 are formed for the greatest surface tension to be measured.

The light barriers 4, 5, 6 consist of known photoelectric scanning devices. The detection of the light barrier signals, the production and counting of time pulses for time measurement so as to detect the drop fractions, the storage of the resultant time counter states Z1 to Z6, the mathematical evaluation of the data and the data output as well as the automation of the entire measurement process are carried out with the air of known electronic components. The important structural groups include control circuit 16 which initiates the measuring process automatically and which carries out the operations needed for this purpose such as, for example, raising and lowering the sample container, sucking the fluid etc., time counter 15, store unit 17, data input and output 25 and computer 24. The four last-mentioned structural groups cooperate with the control circuit 16. In addition to the statement on the measurednumber of drops $T_x$ by means of the input/output unit 25, it is possible to convert it into the physical value of the surface tension (N/m) in the computer 24 by feeding in the density of the sample liquid and the instrument constant via the input and output unit 25. The running time of the liquid between the light barriers 4 and 5 can also be emitted in seconds by the input/output unit 25 in order to monitor the drop formation time.

For quasi continuous measurement, the sample container 7 is replaced by a container through which the liquid to be measured continuously flows. The liquid is, for, example, branched of continuously from the processing stream to be examined. In this way, the stalagmometer according to the invention can be used as an operation gauge.

We claim:
1. An apparatus for automatically determining surface tension by the stalogmometer principle using a pipette containing a test volume and having a drop face at its lower end, comprising a test volume of the pipette defined by an upper light barrier and a lower light barrier, an additional light barrier arranged beneath the drop face, said three light barriers being connected to an evaluation circuit capable of counting the number T0 of whole drops appearing at the drop face upon the flow of the test volume out of said face, said evaluation circuit being comprised of
   (a) an electronic time counter which is connected by circuitry to the three light barriers
   (b) a store in which the following conditions are storable:
      (I) the time counter state Z1 corresponding to the last drop N before the response of the upper light barrier and linked with the meniscus level.

(II) the time counter state Z2 corresponding to the passage of the meniscus through the upper light barrier, (III) the time counter state Z3 being linkable with the meniscus level at the upper light barrier after passage of the next drop N+1, (IV) the number T0 of whole drops detected during the outflow occurring after passage of the drop N+1 from the test volume on the drop face by the light barrier, (V) the time counter state Z4 corresponding to the last drop N+1+T0 before the response of the lower light barrier and being linkable with the meniscus level, (VI) the time counter state Z5 corresponding to the passage of the meniscus level through the lower light barrier, (VII) the time counter state Z6 being linkable with the meniscus level at the lower light barrier after passage of the subsequent drop N+T0+1;

(C) a computer which is capable of forming the quotient $$T_1 = \frac{Z_3 - Z_2}{Z_3 - Z_1} \text{ and } T_2 = \frac{Z_5 - Z_4}{Z_6 - Z_5}$$

from the stored time counter states Z1 to Z6 and then can form the sum $T_x$ of the whole drops TQ and fractions of drops T1 and T2 which are issuable from the test volume so constructed and arranged as to detect fractions of a whole drop whereby the fractions T1, T2 of whole drops pertaining to the test volume during the passage of the liquid meniscus through the upper light barrier and the lower light barrier, from the pulse trains occurring at the three light barrier, are determinable.

2. An apparatus according to claim 1 characterised in that the three light barriers are connected to an electronic control circuit in order to automate the measuring process.

3. An apparatus according to claim 2 characterised in that a flow container through which same liquid continuously flows is arranged beneath the drop face.

* * * * *